United States Patent [19]
Schwartz

[11] Patent Number: 5,972,887
[45] Date of Patent: Oct. 26, 1999

[54] TREATMENT OF INTESTINAL EPITHELIAL CELL MALFUNCTIONS WITH HEPATOCYTE GROWTH FACTOR

[75] Inventor: Marshall Z. Schwartz, Bryn Mawr, Pa.

[73] Assignee: The Nemours Foundation, Wilimington, Del.

[21] Appl. No.: 08/932,391

[22] Filed: Sep. 17, 1997

Related U.S. Application Data

[60] Provisional application No. 60/026,352, Sep. 19, 1996.

[51] Int. Cl.[6] .......................... A61K 38/00; A61K 38/16
[52] U.S. Cl. ................................. 514/12; 514/2
[58] Field of Search ........................................ 514/62, 12

[56] References Cited

FOREIGN PATENT DOCUMENTS 08231418  2/1995  Japan .

OTHER PUBLICATIONS

Zushi et al. Am. J. Physiol.270, G757–G762, Feb. 1996.
Halttunen, T. et al Gastroenterology, 111, 1252–1262, Nov. 1996.
"Importance of fibroblastic support for in vitro differentiation of intestinal endodermal cells and for their response to glucocorticoids" by M. Kedinger, P. Simon–Assmann, E. Alexandre and E. Haffen, *Cell Differentiation*, 20 (1987) 171–182.
"Primary Cultures for Studies of Cell Regulation and Physiology in Intestinal Epithelium", by G. S. Evans, N. Flint, and C. S. Pattern, *Annu. Rev. Physiol.* (1994) 56: 399–417.
"The development of a method for the preparation of rat intestinal epithelial cell primary cultures", by G. S. Evans, N. Flint, A.S. Sobers, B. Eden and C.S. Pattern, *Journal of Cell Science*, 101 (1992) 219–231.
"Characterization of isolated duodenal epithlial cells along a crypt–villus axis in rats fed diets with different iron content", by Phillip S. Oates, Carla Thomas and Evan H. Morgan *Journal of Gastroenterology and Hematology*, (1997) 12: 829–838.
Taylor, R. et al., Hepatocyte growth factor gene expression after massive small bowel resection: lack of stimulation in lung and liver, *Experimental and Clinical Endocrinology & Diabetes*, 103, (1995) 58–62.
Seki, T. et al.,, Organization of the human hepatocyte growth factor–encoding gene, *Gene*, Elsevier Science Publishers B.V. 102 (1991) 213–219.
Tashiro, K. et al., Deduced primary structure of rat hepatocyte growth factor and expression of the mRNA in rat tissues, *Proc. Natl. Acad. Sci. USA*, vol. 87, pp. 3200–3204, Apr. 1990, Cell Biology.
Matsumoto, K., et al., Hepatocyte Growth Factor: Molecular Structure, Roles in Liver Regeneration, and Other Biological Functions, *Critical Reviews in Oncogenesis*, 3(1,2):27–54 (1992).
Dignass, A. U., et al., Hepatocyte Growth Factor/Scatter Factor Modulates Intestinal Epithlial Cell Proliferation and Migration, *Biochemical and Biophysical Research Communications*, vol. 2020, No. 2, Ju. 29, 1994, pp. 701–709.

Oka, M. et al., Hepatocyte Growth Factor Region Specifically Stimulates Gastro–intestinal Epithelial Growth Primary Culture, (Abstract), *AGA Abstracts, Gastroenterology* vol. 108, No. 4.
Tsuji, S. et al., Roles of Hepatocyte Growth Factor and Its Receptor in Gastric Musocas, A Cell Biologicla and Molecular Biological Study, *Digestive Disease and Sciences*, vol. 40, No. 5 (May 1995) pp. 1132–1139.
Fukamachi, H. et al., Hepatocyte Growth Factor Region Specifically Stimulates Gastro–intestinal Epithelial Growth in Primary Culture, *Biochemical and Biophysical Research Communications*, vol. 205, No. 2, Dec. 15, 1994, pp. 1445–1451.
Zamegar, R., et al., Tissue distribution of hepatopoietin–A: A heparin–binding polypeptide growth factor for hepatocytes, *Proc. Natl. Acad. Sci. USA*, vol. 87, pp. 1252–1256, Feb. 1990, Cell Biology.
Nakamura, T., et al., Partial Purification and Characterization of Hepatocyte Growth Factor from Serum of Hepatectomized Rats, *Biochemical and Biophysical Research Communications*, vol. 122, No. 3, Aug. 16, 1984, pp. 1450–1459.
Russell, W.E., et al., Partial Characterization of a Hepatocyte Growth Factor From Rat Platelets, *Journal of Cellular Physiology*, 119:183–192 (1984).
Biosis Abstract No. 99090063 Liu X–L, et al., *Cancer Research* 56 (14) 1996 3371–3379.
Biosis Abstract No. 99052390, Zushi, S. et al., American Journal of Physiology 270 (5 part 1) 1996, G757–G762.
Biosis Abstract No. 99021608, Sunitha, I., et al., 96th Annual Meeting of the American Gastroenterological Association and the Digestive Disease Week, San Francisco, CA USA May 19–22, 1996.
Biosis Abstract No. 98730306 Sirica, A.E., Toxicologic Pathology, 24 (1) 1996, 90–99.
Biosis Abstract No. 98682224, Huff, J.L., et al., Oncogene 12(2) 1996, 299–307.
Biosis Abstract No. 98536833, Kar, S., et al., 46th Annual Meeting and Postgraduate Course of the American Association for the Study of Liver Diseases, Chicago, IL, Nov. 3–7, 1995.
Biosis Abstract No. 98310316 Tsuji, S. et al., Digestive Diseases and Sciences, 40 (5) 1995, 1132–1139.
Biosis Abstract No. 98294826, Oka, M., et al., 95th Meeting of the American Gastroenterological Association and Digestive Disease Week, San Diego, CA, USA, May 14–17, 1995.
Biosis Abstract No. 98266786, Taylor, R., et al., Experimental and Clinical Endocrinology & Diabetes, 103 (1) 1995, 58–62.

(List continued on next page.)

*Primary Examiner*—Cecilia J. Tsang
*Assistant Examiner*—Michael Borin
*Attorney, Agent, or Firm*—McGuire, Woods, Battle and Boothe LLP

[57] ABSTRACT

Reversal of reduced intestinal mucosal mass and absorptive function in patients by the administration of low doses of exogenous HGF either systemically or intraluminally.

18 Claims, 3 Drawing Sheets

OTHER PUBLICATIONS

Biosis Abstract No. 98211012, Sirica, A.E., et al., Experimental Biology 95, Part II, Atlanta, GA USA Apr. 9–13, 1995.

Biosis Abstract No. 98199668, Sirica, A.E., et al., Eighty–sixth Annual Meeting of the American Association for Cancer Research, Toronto, Canada, Mar. 18–22, 1995.

Biosis Abstract No. 98118952, Wang, Y., Journal of Anatomy, 185 (3) 1994, 543–551.

Biosis Abstract No. 98089804 Fukamachi, H., Biochemical and Biophysical Research Communications 205 (2) 1994, 1445–1451.

Biosis Abstract No. 98003083, Kawakami, S, et al., Hepatology, 20 (5) 1994, 1255–1260.

Biosis Abstract No. 97426580, Shinozuka, H., et al., Laboratory Investigation, 71 (1) 1994, 35–41.

Biosis Abstract No. 97415869, Dignass, A.U., et al. Biochemical and Biophysical Research Communications 202 (2) 1994, 701–709.

Biosis Abstract No. 97299058, Odedra, R.M., et al., 95tyh Annual Meeting of the American Gastroenterological Association, New Orleans, LA, USA, May 15–18, 1994.

Biosis Abstract No. 97281074, Nusrat, A., et al., Journal of Clinical Investigation, 93 (5) 1994, 2056–2065.

Biosis Abstract no. 97220852, Sunitha, I., et al., Clinical and Experimental Metastasis 12 (2) 1994, 143–154.

Biosis Abstract no. 97165631 Fukamachi, H., et al., 64th Annual Meeting of the Zoological Society of Japan, Okinawa, Japan, Nov. 20–23–1993.

Biosis Abstract No. 96063267, Huff, J.L., et al., Proceedings of the National Academy of Sciences of the United States of America 90 (13) 1993, 6140–6144.

Biosis Abstract No. 45017504, Wang, Y., 94th Annual Meeting of the American Gastoenterological Association, Boston, MA, USA, May 15–21, 1993. Gastroenterology 104 (SuppL.) 1993, A288.

Biosis Abstract No. 45017426, Nusrat, A., et al., 94th Anuual Meeting of the American Gastroenterological Association, Boston, MA, USA, May 15–21, 1993, Gastroenterology 104 (4 SuppL.) 1993, A269.

Biosis Abstract No. 42032235, Takahshi, N., et al., Naturwissenschaften 78 (10) 1991 457–459.

* p < 0.05

TREATMENT OF INTESTINAL EPITHELIAL CELL MALFUNCTIONS WITH HEPATOCYTE GROWTH FACTOR

This is a regular patent application based on provisional application P60/026,352, filed Sep. 19, 1996.

BACKGROUND OF THE INVENTION

The invention relates in general to the treatment of intestinal epithelial cell syndromes in humans characterized by reduced absorption of foodstuffs by intestinal cells. More particularly, the invention relates to stimulation of epithelial cell growth and function in the small intestine of patients requiring same by treatment with with Hepatocyte Growth Factor ("HGF").

The etiology of inadequate intestinal absorption includes: loss due to development abnormalities such as intestinal atresias and in utero midgut volvus; postnatal loss from surgical resection after infarction (midgut volvulus or vascular occlusion), trauma or tumor; inflammation, such as is due to infection (necrotizing enterocolitis and acute gastroenteritis) and autoimmune etiologies such as in Crohn's Disease and ulcerative colitis.

Many of the conditions result in "Short Bowel Syndrome" ("SBS"), the expression applied to syndromes that occur following extensive resection of the small intestine. The main consequence of SBS is malabsorption, which leads to malnutrition, dehydration, and potentially lethal metabolic alterations. The severity of the syndrome is determined by the length of functional small intestine remaining after resection. The adaptive response of the remaining intestine is the crucial factor in the subsequent quality of life of such patients. altered motility, resulting in increased luminal absorptive ability. However, this adaptive response is frequently insufficient to allow for sufficient enteral nutrition.

To better the quality of life of the aforementioned patients, it is essential to increase the capacity for absorption of the remaining small intestine. It follows, therefore, that there is an important need for agents to stimulate the functioning and numbers of the remaining epithelial cells lining the small intestine in such disorders.

Regeneration of the liver in experimental animals after partial hepatectomy or liver injury is believed to be due, at least in part, to the effects of HGF on hepatocytes. HGF is a heterodimeric, heparin-binding protein composed of heavy $\alpha$ and light $\beta$ chains of molecular weights of 70 kDa and 35 kDa, respectively, that is known to stimulate the growth, i.e., DNA synthesis, of hepatocytes in tissue culture. Matsumoto et al., *Crit. Revs. Oncogen.* 3: 27 (1992).

Recent studies have demonstrated that HGF stimulates the growth, not only of hepatocytes in culture, but also of intestinal crypt (IEC-6) epithelial cells in vitro. Dignass et al., *Biochem. Biophys. Res. Commun.* 202: 701 (1994). In addition, it has been demonstrated that the expression of HGF and HGF receptor (c-MET) genes can occur in the gastrointestinal tract, lung, kidney, brain, thymus and pancreas. Based on such studies, it has been speculated that HGF is a mesenchymal cell-derived growth factor that acts on epithelial cells through paracrine and endocrine mechanisms to achieve cell growth. Matsumoto et al. (1992), above.

Despite these speculations, it is not known whether HGF has cell growth and increased cell function effects on intestinal epithelial cells in vivo, that is, whether HGF, administered systemically or intraluminally to animals suffering from intestinal malabsorption due to reduced epithelial cell number and function, e.g., in SBS, would increase the numbers and functional activity of the epithelial cells of the remaining small intestine sufficient to reverse intestinal malabsorption in such subjects.

It is an object of this invention to use HGF in vivo to increase the functional (i.e., absorptive) capacity of small intestinal epithelial cells remaining following the institution of intestinal malabsorption as a result of mass reduction or functional reduction of a portion of the small bowel.

SUMMARY OF THE INVENTION

The aforementioned object has been achieved by the discoveries that HGF enhances DNA synthesis in IEC-6 cells in vitro, that HGF given systemically or intraluminally enhances absorption of carbohydrate and amino acids in vivo in normal rat small intestine, that HGF increases mucosal mass in vivo when given intraluminally or systemically, that HGF, administered following massive small bowel resection, further increases carbohydrate and amino acid absorption beyond the normal adaptive response, that HGF, administered after massive small bowel resection, increases mucosal mass beyond the normal adaptive response, and that these effects of HGF persist at least three weeks following cessation of administration of the drug.

In further embodiments of the invention, the administration of HGF in vivo is useful in treating a variety of disorders involving the small intestine, including loss of absorptive function due to developmental abnormalities, postnatal loss from surgical resection of a portion of the small intestine, or restorating mucosal function following inflammatory processes due to infection or an autoimmune etiology, or combinations of these processes.

DETAILED DESCRIPTION OF THE PREFERRED EMBODIMENTS

Figure 1:
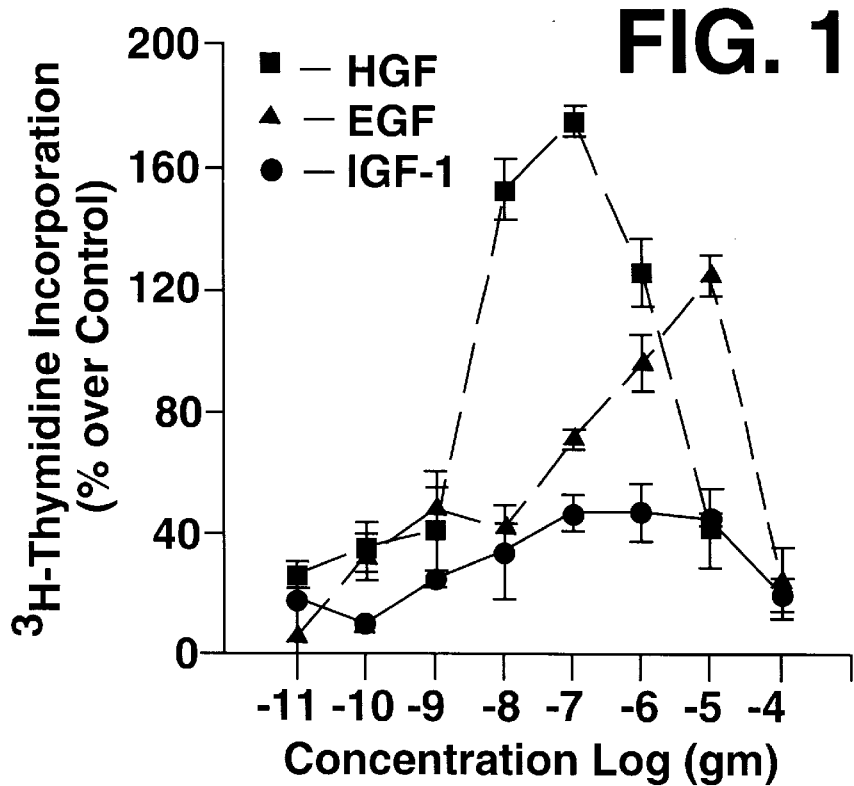
FIG. 1 shows the effects of HGF, insulin-like growth factor-1 (IGF-1), and epidermal growth factor (EGF) on the proliferation of epithelial cells (IEC-6) as determined by measuring DNA synthesis from labeled thymidine.

It has been discovered that HGF is a potent growth factor for intestinal epithelial cells both in vitro and in vivo, and that this action is not synergistic with the effects of IGF-1 or EGF on such cells.

Importantly, it has been discovered that HGF enhances intestinal mucosal mass (DNA and protein content) and carbohydrate and amino acid absorption function when delivered either systemically (intravenously) or intraluminally in an in vivo normal rat model at a level of about 30–300 $\mu$g of HGF per kg body weight per day.

It has been unexpectedly discovered that HGF, at dosage ranges of from about 30 to 300 $\mu$g/kg body weight/day, enhances intestinal epithelial cell function (absorption of hexoses and amino acids) and intestinal mucosal mass beyond the normal adaptive response in a rat in vivo model of reduced epithelial function and mass produced by massive resection of the small bowel (Short Bowel Syndrome). Intraluminal administration of HGF is more effective than systemic administration of the drug in all parameters tested (galactose absorption, glycine absorption, DNA content and protein content of remaining intestinal mucosal tissue). Importantly, these effects of HGF persist for at least three weeks after treatment with HGF has stopped, which has clinical implications.

The facts that HGF can enhance DNA synthesis in IEC-6 epithelial cell cultures independently of IGF-1 or EGF, and can significantly increase carbohydrate and amino acid absorption and mucosal mass when given in vivo to normal rats or to a rat model of impaired small bowel function indicates that HGF is useful for human patients with inadequate intestinal absorption presenting, for example, with:

1. Loss due to developmental abnormalities
   a. intestinal atresia
   b. in utero midgut volvus
2. Postnatal loss from surgical resection
   a. infarction (midgut volvulus or vascular occlusion)
   b. trauma
   c. tumor
3. Inflammatory
   a. infection
      (i) necrotizing enterocolitis
      (ii) acute gastroenteritis (e.g., cholera)
   b. Autoimmune
      (i) Crohn's Disease
      (ii) ulcerative colitis HCG can be administered to patients at effective doses and for effective periods by the intestinal intraluminal route (catheter or sustained release preparations) or by a systemic route (e.g., intravenously). Carriers for HCG may be found in Remington's Pharmaceutical Sciences, 18th ed., 1990, Mack Publishing Co., Easton, Pa.

The great advantage of the administration of HGF (systemically or intraluminally) would be to allow patients who are dependent on intravenous calories to obtain adequate nutrition enterally following the enhanced absorption brought about by HGF. This would allow these patients to avoid the very high costs, complications, and poor quality of life associated with parenteral nutrition.

The following examples are designed merely to provide exemplification of the preferred embodiments of the invention, and should not be construed as providing any limitation on the scope of the invention which is described in the specification and the appended claims.

EXAMPLES

Example 1
In Vitro Studies
IEC-6 epithelial cells were seeded into 96-well plates in serum free DMEM growth medium supplemented with 0.1 IU insulin/ml. Twenty four hours later, varying concentrations of HGF, IGF-1 or EGF were added to the wells. After a 20-hour period of incubation, cells were exposed to $^3$H-thymidine (1 $\mu$Ci/well) for another 4 hours. Cells, harvested by a PHD Cell Harvester (Cambridge Technology, Mass.), were analyzed for radioactivity as an estimate of DNA synthesis (i.e., cell growth). The data are shown in FIGS. 1 and 2.

Figure 2:
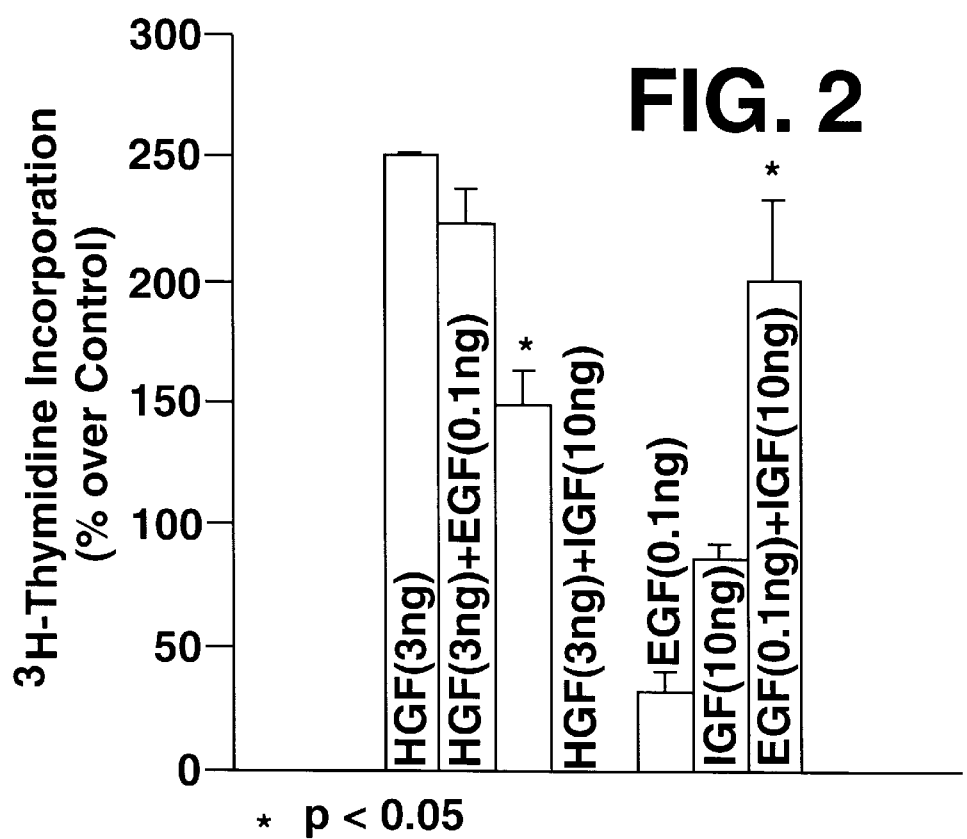
FIG. 2 shows the effects of combinations of HGF, IGF-1 and EGF on proliferation of IEC-6 cells.

The data of FIG. 1 show that HGF produced the greatest increase (175%) on DNA synthesis ($p<0.001$) and produced a typical dose-response curve. IGF-1 produced only a 47% increase ($p<0.001$), and EGF a 125% increase ($p<0.001$) in DNA synthesis compared to control. IGF-1 inhibited the effect of HGF ($p<0.05$), whereas EGF and IGF-1 were synergistic when tested together (FIG. 2). These results indicate that HGF is a highly potent growth factor for intestinal epithelial cells.

Example 2
In Vivo Effects of HGF on Small Intestinal Function and Tissue Mass Adaptation
Sprague-Dawley rats (175–225 g) were systemically infused using osmotic minipumps (Model 2002, Alza, Palo Alto, Calif.) that are designed to deliver their contents at a constant rate, for 14 days. The pumps are filled with an isotonic solution of HGF so as to deliver 75, 150 or 300 $\mu$g of the drug/kg body weight/day. The pumps were placed subcutaneously and attached to PE-60 polyethylene catheters (Clay-Adams, Parsippany, N.J.) that were inserted into the internal jugular vein.

Osmotic pumps were also used for the luminal perfusions. In such experiments, catheters were inserted into the intestinal lumen about 12 cm proximal from the midpoint of the small intestine. The pumps were tunneled subcutaneously to the back of the rat where they were connected to the osmotic pumps delivering HGF as above. Groups of ten animals were used for controls and for each concentration of HGF, for both systemic and luminal systems.

A. Absorption
In both systemic and luminal perfusion animals, the 10 cm segments proximal and distal to the midintestine were isolated for absorption studies.

Twelve gauge polyethylene catheters were placed in each end of the intestinal segment to establish a closed loop recirculation perfusion system. Catheters were secured at both ends to form water-tight seals. The other ends of the catheters were submerged into a reservoir containing the perfusate. A roller pump was used to deliver a continuous perfusion at 3 ml/h for 4 h. The perfusate consisted of either $C^{14}$-galactose (1 $\mu$Ci/10 ml) or $C^{14}$-glycine (1 $\mu$Ci/10 ml) added to their respective unlabeled 5 mM stock solutions prepared in PBS. Each perfusate also contained $^3$H-inulin (5 $\mu$Ci/10 ml) as a nonabsorbable marker to function as an internal control for loss of substrate by processes other than absorption.

Triplicate 0.1 ml samples were collected from the perfusion reservoirs at 0, 0.5, 1, 2, 3, 4 hour intervals and the radioactivities determined by LSS. Absorption of substrates were determined by the disappearance of counts from the reservoirs expressed as micromoles of substrate absorbed per $cm^2$ of intestine.

B. DNA Concentration
Following the absorption studies, biopsy specimens of the small intestine were collected for determination of DNA concentrations. The method used was the diphenylamine procedure of Giles et al., Nature 206:93 (1965), which is incorporated herein by reference. DNA concentrations are expressed as $\mu$g DNA/mg intestinal mucosa.

C. Results
The results for mucosal substrate absorption, DNA content and protein mass, following systemic administration of HGF, are shown in Table 1 below. In the table, Control represents normal saline. In the 3 experimental groups, HGF was systemically administered at levels of 75 $\mu$g/kg body weight/day, 150 $\mu$g/kg/day, and 300 $\mu$g/kg/day. In this study, 5 animals were used in each group. Substrates were infused for 14 days.

A similar study was performed, but with HGF being administered intraluminally. The results are shown in Table 2.

Figure 3:
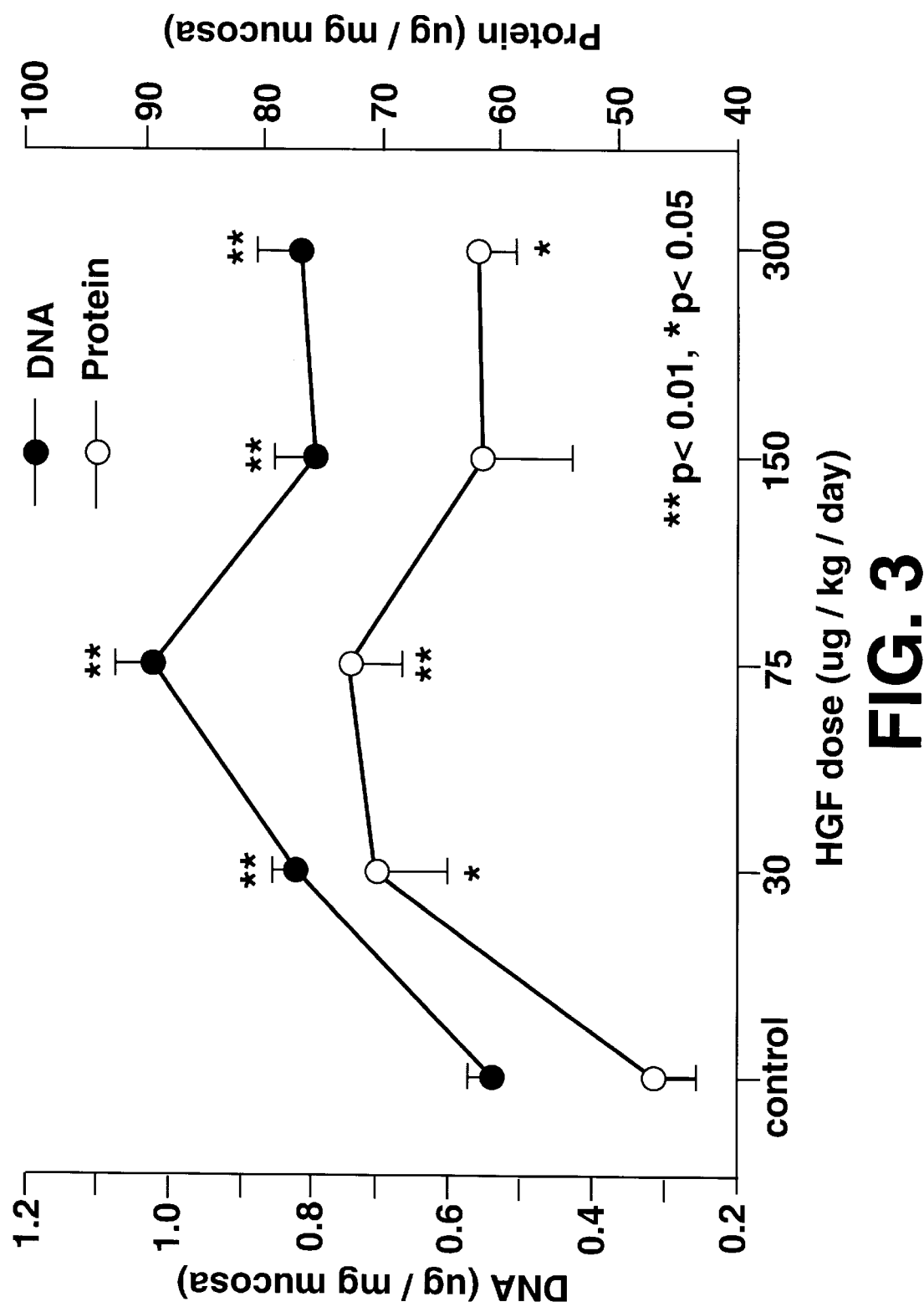
FIG. 3 shows the in vivo effects of luminal administration of HGF on intestinal mucosal mass (i.e., DNA and protein content.
Figure 4:
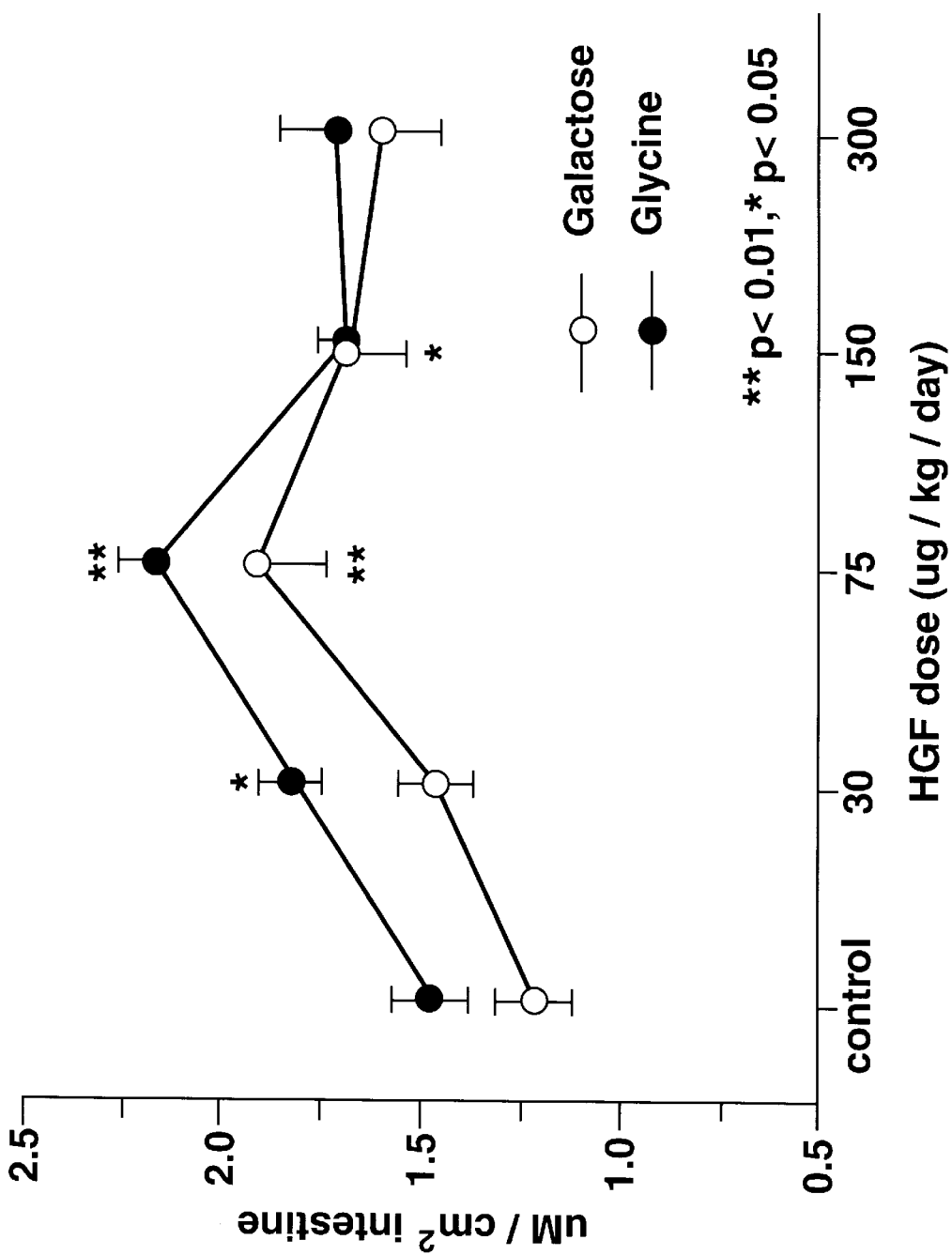
FIG. 4 shows the effects of in vivo administration of HGF on the function (i.e., galactose and glycine absorption) of intestinal epithelial cells.

Dose-effect curves for the effects of HGF administered intraluminally are shown more dramatically by the data of FIGS. 3 (galactose and glycine absorption) and 4 (DNA and protein content). It is evident that the optimal dosage level for HGF in these luminal experiments is at about 75 μg/kg body weight/day, but that the effective dosage range is at least as low as 30 μg and as high as 300 μg of the drug/kg body weight/day.

These data demonstrate for the first time that HGF administered either systemically or intraluminally can increase intestinal epithelial cell function and stimulate cell proliferation in normal animals.

Example 3

Effects of HGF on Short Bowel Syndrome in a Rat Model

Sprague-Dawley rats (175–225 g body weight) underwent an 80% small intestine resection, and insertion of catheters as described in Example 2 above. Two weeks later the catheters were connected to osmotic pumps as described above. Five groups of 10 animals each were used, as described below:

A. Systemic saline control;

B. HGF to deliver 150 μg/kg/day systemically for 14 days;

C. Intraluminal saline control;

D. HGF to deliver 75 μg of drug/kg/day intraluminally.

Absorption and DNA studies were carried out as in Example 2. The data are shown in Table 3.

The data demonstrate that HGF significantly increased galactose and glycine intestinal absorption, tissue DNA content, protein content, galactose and glycine absorption as a function of DNA concentration, DNA as a function of intestinal surface area, and protein as a function of intestinal surface area. Further, in each parameter, introduction of HGF directly into the lumen was substantially more efficient than using the systemic route.

These unexpected results demonstrate for the first time that, in an in vivo rat model of inadequate intestinal mucosal mass and function in human patients, administration of low doses of HGF provided significant reversal of the malabsorption syndrome such as is also exhibited by human patients.

While applicant is not bound by any particular mechanism of action of HGF, it may be significant that HGF upregulates the gene expression of two glucose transporter proteins following massive bowel resection.

TABLE 1

In Vivo Systemic (Normal Rat) Study

| | Control | HGF 75 μg/kg/day | HGF 150 μg/kg/day | HGF 300 μg/kg/day |
|---|---|---|---|---|
| Galactose Abs ($\mu M/cm^2$) | 1.21 SE 0.07 | 2.07 SE 0.17 (70%) $p < 0.01$ | 2.39 SE 0.04 (97%) $p < 0.01$ | 1.86 SE 0.17 (53%) $p < 0.01$ |
| Glycine Abs ($\mu M/cm^2$) | 1.62 SE 0.04 | 2.27 SE 0.23 (40%) $p < 0.05$ | 1.97 SE 0.09 (22%) $p < 0.01$ | 1.79 SE 0.13 (11%) $p = NS$ |
| DNA content ($\mu M/mg$ mucosa) | 0.49 SE 0.03 | 0.73 SE 0.04 (49%) $p < 0.01$ | 0.85 SE 0.06 (73%) $p < 0.01$ | 0.89 SE 0.02 (82%) $p < 0.01$ |
| Protein Content ($\mu g/mg$ mucosa) | 42.6 SE 1.1 | 56.4 SE 5.0 (33%) $p < 0.05$ | 64.2 SE 4.6 (51%) $p < 0.01$ | 60.4 SE 2.8 (42%) $p < 0.01$ |
| mg mucosa/$cm^2$ surface area | 22.4 SE 1.1 | 30.1 SE 2.8 (33%) $p < 0.05$ | 29.7 SE 3.1 (33%) $p = NS$ | 26.1 SE 1.5 (17%) $p = NS$ |
| Galactose Abs/DNA ($\mu M/mg$ DNA) | 130.4 SE 12.9 | 84.6 SE 11.7 | 128.4 SE 25.7 | 80.8 SE 6.7 |
| Glycine Abs/DNA ($\mu g/mg$ DNA) | 151.6 SE 16.3 | 109.8 SE 17.3 | 100.8 SE 19.7 | 79.4 SE 8.8 |
| DNA $\mu g/cm^2$ surface area | 11.4 SE 0.4 | 2.1 SE 2.9 (94%) $p < 0.01$ | 24.5 SE 3.5 (115%) $p < 0.01$ | 23.0 SE 1.3 (102%) $p < 0.01$ |
| Protein mg/$cm^2$ surface area | 0.92 SE 0.05 | 1.52 SE 0.11 (65%) $p < 0.01$ | 1.79 SE 0.28 (95%) $p < 0.05$ | 1.59 SE 0.17 (73%) $p < 0.01$ |

( ) = % increase compare to control

TABLE 2

Luminal (Normal Rat) Study

|  | Control | HGF 30 μg/kg/day | HGF 75 μg/kg/day | HGF 150 μg/kg/day | HGF 300 μg/kg/day |
|---|---|---|---|---|---|
| Galactose Abs ($\mu$M/cm$^2$) | 1.22 SE 0.09 | 1.46 SE 0.09 (20%) | 1.91 SE 0.17 (57%) $p < 0.01$ | 1.69 SE 0.15 (39%) $p < 0.05$ | 1.60 SE 0.15 (31%) |
| Glycine Abs ($\mu$M/cm$^2$) | 1.48 SE 0.10 | 1.83 SE 0.08 (24%) $p < 0.05$ | 2.17 SE 0.10 (47%) $p < 0.01$ | 1.69 SE 0.07 (14%) | 1.72 SE 0.14 (16%) |
| DNA content ($\mu$g/mg mucosa) | 0.54 SE 0.03 | 0.82 SE 0.03 (52%) $p < 0.01$ | 1.02 SE 0.05 (89%) $p < 0.01$ | 0.79 SE 0.06 (46%) $p < 0.01$ | 0.81 SE 0.06 (50%) $p < 0.01$ |
| Protein Content ($\mu$g/mg mucosa) | 47.3 SE 3.8 | 70.9 SE 6.4 (50%) $p < 0.05$ | 72.8 SE 4.4 (54%) $p < 0.01$ | 61.7 SE 7.8 (30%) $p = NS$ | 61.9 SE 3.0 (31%) $p < 0.05$ |
| mg mucosa/cm$^2$ surface area | 24.2 SE 0.8 | 23.2 SE 1.2 $p = NS$ | 36.7 SE 3.7 (52%) $P = 0.01$ | 33.4 SE 2.8 (38%) $P = 0.013$ | 31.0 se 3.2 (28%) $P = 0.075$ |
| Galactose Abs/DNA ($\mu$M/mg DNA) | 89.3 SE 14.6 | 77.1 SE 5.7 | 53.1 SE 6.7 $p = 0.054$ | 66.0 SE 7.3 | 65.2 SE 2.1 |
| Glycine Abs/DNA ($\mu$M/mg DNA) | 110.2 SE 22.0 | 96.9 SE 6.1 | 60.3 SE 6.4 $p = 0.06$ | 65.6 SE 4.0 | 71.7 SE 7.5 |
| DNA $\mu$g/cm$^2$ surface area | 13.8 SE 0.8 | 19.0 SE 0.7 (38%) $p < 0.01$ | 37.8 SE 4.9 (174%) $p < 0.01$ | 25.9 SE 1.2 (88%) $p < 0.01$ | 24.5 SE 1.8 (78%) $p < 0.01$ |
| Protein mg/cm$^2$ surface area | 1.35 SE 0.13 | 1.60 SE 0.07 (19%) $p = NS$ | 2.52 SE 0.25 (87%) $p < 0.01$ | 2.01 SE 0.18 (49%) $p < 0.05$ | 1.96 SE 0.19 45% $p < 0.05$ |

( ) = % increase compare to control

TABLE 3

In Vivo Short Bowel Study

|  | Systemic | | Luminal | |
|---|---|---|---|---|
|  | Control | HGF 150 μg/kg/day | Control | HGF 75 μg/kg/day |
| Galactose Abs ($\mu$M/cm$^2$) | 1.23 SE 0.10 | 2.07 SE 0.29 (68%) $p < 0.05$ | 1.33 SE 0.07 | 2.85 SE 0.24 (114%) $p < 0.01$ |
| Glycine Abs ($\mu$M/cm$^2$) | 1.24 SE 0.23 | 1.95 SE 0.09 (57%) $p < 0.05$ | 1.06 SE 0.08 | 2.40 SE 0.33 (126%) $p < 0.01$ |
| DNA content ($\mu$g/mg mucosa) | 0.65 SE 0.02 | 0.76 SE 0.03 (17%) $p < 0.01$ | 0.68 SE 0.02 | 0.90 SE 0.05 (32%) $p < 0.01$ |
| Protein Content ($\mu$g/mg mucosa) | 59.2 SE 3.2 | 92.9 SE 5.8 (57%) $p < 0.01$ | 66.9 SE 0.91 | 96.7 SE 4.7 (45%) $p < 0.01$ |
| mg mucosa/cm$^2$ surface area | 40.4 SE 2.2 | 41.0 SE 0.7 $p = NS$ | 38.4 SE 2.0 | 42.8 SE 0.9 (11%) $p = NS$ |
| Galactose Abs/DNA ($\mu$M/mg DNA) | 54.7 SE 4.2 | 69.7 SE 13.8 (27%) $p = NS$ | 49.5 SE 4.6 | 76.3 SE 12.2 (54%) $p = 0.073$ |
| Glycine Abs/DNA ($\mu$M/mg DNA) | 50.7 SE 9.8 | 62.3 SE 4.1 (23%) $p = NS$ | 39.2 SE 4.3 | 62.9 SE 10.8 (60%) $p = 0.077$ |
| DNA $\mu$g/cm$^2$ surface area | 24.9 SE 1.1 | 30.8 SE 0.7 (24%) $p < 0.01$ | 25.6 SE 0.9 | 36.1 SE 2.6 (41%) $p < 0.01$ |
| Protein mg/cm$^2$ surface area | 2.45 SE 0.19 | 3.74 SE 0.20 (53%) $p < 0.01$ | 2.66 SE 0.09 | 3.69 SE 0.12 (39%) $p < 0.01$ |
| surface area | | $p < 0.01$ | | $p < 0.01$ |

( ) = % increase compare to control

What is claimed is:

1. A method of increasing intestinal mucosal substrate absorptive functions and intestinal tissue mass of a small intestine beyond the normal adaptive response in a subject wherein said subject has a condition selected from the group consisting of Short Bowel Syndrome, a developmental abnormality of the small intestine, a surgical resection of the small intestine, an intestinal inflammatory process, a condition characterized by inadequate intestinal mass, and a condition characterized by inadequate intestinal absorption, the method comprising administering to said subject an effective dose of Hepatocyte Growth Factor ("HGF") in a pharmaceutically effective vehicle.

2. The method of claim 1 wherein said HGF is administered to said subject systemically or into the intestinal lumen.

3. The method of claim 1, wherein said HGF is administered at a dosage level of about 30–300 μg/kg body weight/day.

4. The method of claim 1 wherein said increase in intestinal mucosal substrate absorptive functions in said subject persists for at least about three weeks following the cessation of HGF administration.

5. The method of claim 1 wherein said increase in intestinal tissue mass in said subject persists for at least about three weeks following the cessation of HGF administration.

6. The method of claim 1 wherein said increase in intestinal mucosal substrate absorptive functions and said increase in intestinal tissue mass of a small intestine persist for at least about three weeks following the cessation of HGF administration.

7. A method of increasing intestinal mucosal substrate absorptive functions of a small intestine beyond the normal adaptive response in a subject wherein said subject has a condition selected from the group consisting of Short Bowel Syndrome, a developmental abnormality of the small intestine, a surgical resection of the small intestine, an intestinal inflammatory process, a condition characterized by inadequate intestinal mass, and a condition characterized by inadequate intestinal absorption, the method comprising administering to said subject an effective dose of Hepatocyte Growth Factor ("HGF") in a pharmaceutically effective vehicle.

8. The method of claim 7 wherein said HGF is administered to said subject systemically or into the intestinal lumen.

9. The method of claim 7 wherein said HGF is administered at a dosage level of about 30–300 µg/kg body weight per day.

10. A method of increasing intestinal mucosal substrate absorptive functions of a small intestine in a subject wherein said subject has a condition selected from the group consisting of Short Bowel Syndrome, a developmental abnormality of the small intestine, a surgical resection of the small intestine, an intestinal inflammatory process, a condition characterized by inadequate intestinal mass, and a condition characterized by inadequate intestinal absorption, the method comprising administering to said subject an effective dose of Hepatocyte Growth Factor ("HGF") in a pharmaceutically effective vehicle wherein said increase in intestinal mucosal substrate absorptive functions in said subject persists for at least about three weeks following the cessation of HGF administration.

11. The method of claim 10 wherein said HGF is administered to said subject systemically or into the intestinal lumen.

12. The method of claim 10 wherein said HGF is administered at a dosage level of about 30–300 µg/kg body weight per day.

13. A method of increasing intestinal tissue mass of a small intestine beyond the normal adaptive response in a subject wherein said subject has a condition selected from the group consisting of Short Bowel Syndrome, a developmental abnormality of the small intestine, a surgical resection of the small intestine, an intestinal inflammatory process, a condition characterized by inadequate intestinal mass, and a condition characterized by inadequate intestinal absorption, the method comprising administering to said subject an effective dose of Hepatocyte Growth Factor ("HGF") in a pharmaceutically effective vehicle.

14. The method of claim 13 wherein said HGF is administered to said subject systemically or into the intestinal lumen.

15. The method of claim 13 wherein said HGF is administered at a dosage level of about 30–300 µg/kg body weight per day.

16. A method of increasing intestinal tissue mass of a small intestine in a subject wherein said subject has a condition selected from the group consisting of Short Bowel Syndrome, a developmental abnormality of the small intestine, a surgical resection of the small intestine, an intestinal inflammatory process, a condition characterized by inadequate intestinal mass, and a condition characterized by inadequate intestinal absorption, the method comprising administering to said subject an effective dose of Hepatocyte Growth Factor ("HGF") in a pharmaceutically effective vehicle wherein said increase in intestinal tissue mass persists for at least about three weeks following the cessation of HGF administration.

17. The method of claim 16 wherein said HGF is administered to said subject systemically or into the intestinal lumen.

18. The method of claim 16 wherein said HGF is administered at a dosage level of about 30–300 µg/kg body weight per day.

* * * * *